(12) United States Patent
Tarabichi et al.

(10) Patent No.: US 10,159,493 B2
(45) Date of Patent: Dec. 25, 2018

(54) REVISION JOINT REPLACEMENT DEVICE AND METHOD

(71) Applicant: Zimmer, inc., Warsaw, IN (US)

(72) Inventors: Samih Tarabichi, Dubai (AE); Mohamed M. Elfekky, Dubai (AE)

(73) Assignee: Zimmer, Inc., Warsaw, IN (US)

( * ) Notice: Subject to any disclaimer, the term of this patent is extended or adjusted under 35 U.S.C. 154(b) by 499 days.

(21) Appl. No.: 14/591,534

(22) Filed: Jan. 7, 2015

(65) Prior Publication Data

US 2015/0190143 A1 Jul. 9, 2015

Related U.S. Application Data

(60) Provisional application No. 61/925,305, filed on Jan. 9, 2014.

(51) Int. Cl.
*A61B 17/15* (2006.01)
*A61B 17/80* (2006.01)
(Continued)

(52) U.S. Cl.
CPC .......... *A61B 17/154* (2013.01); *A61B 17/155* (2013.01); *A61B 17/157* (2013.01);
(Continued)

(58) Field of Classification Search
CPC . A61B 17/154–17/157; A61B 17/1764; A61B 17/1717
See application file for complete search history.

(56) References Cited

U.S. PATENT DOCUMENTS 6,510,334 B1 1/2003 Schuster et al.
8,066,708 B2 11/2011 Lang et al.
(Continued)

FOREIGN PATENT DOCUMENTS

CN 106132321 A 11/2016
EP 0947169 A2 10/1999
(Continued)

OTHER PUBLICATIONS

"European Serial No. 15701866.4, Response Filed Mar. 23, 2017 to communication pursuant to Rules 161(1) and 162 EPC dated Sep. 13, 2016", 18 pgs.
(Continued)

*Primary Examiner* — Olivia C Chang
(74) *Attorney, Agent, or Firm* — Schwegman Lundberg & Woessner, P.A.

(57) ABSTRACT

A device to aid in performing a revision surgery on a joint can comprise: a body member having a bone facing bottom surface, an opposing top surface, a first end portion configured to be disposed on a bone, and a second end portion opposite the first end portion and configured to be disposed on the bone nearer to the joint relative to the first end portion; a connecting member attached to the body member and configured to extend beyond an end of the bone; and a guide member attached to the connecting member and including an opening configured to receive a cutting tool. The device can be sized and shaped based on a computed tomography scan of the bone, and the guide member can be configured so that when the device is installed on the bone, the longitudinal axis of the opening is aligned with a longitudinal direction of the bone.

21 Claims, 11 Drawing Sheets

(51) Int. Cl.
*A61B 17/17* (2006.01)
*A61F 2/38* (2006.01)
*A61B 17/56* (2006.01)
*A61F 2/30* (2006.01)

(52) U.S. Cl.
CPC ...... *A61B 17/1764* (2013.01); *A61B 17/8061* (2013.01); *A61F 2/3859* (2013.01); *A61B 2017/564* (2013.01); *A61B 2017/567* (2013.01); *A61B 2017/568* (2013.01); *A61F 2002/30948* (2013.01)

(56) References Cited

U.S. PATENT DOCUMENTS

| | | | |
|---|---|---|---|
| 2009/0254093 | A1 | 10/2009 | White et al. |
| 2011/0015639 | A1* | 1/2011 | Metzger ............... A61B 17/175 606/91 |
| 2014/0025348 | A1 | 1/2014 | Abiven |
| 2015/0032113 | A1* | 1/2015 | Anderson .......... A61B 17/1764 606/88 |

FOREIGN PATENT DOCUMENTS

| | | |
|---|---|---|
| GB | 2447702 A | 9/2008 |
| WO | WO-2013136302 A1 | 9/2013 |
| WO | WO-2015105855 A1 | 7/2015 |

OTHER PUBLICATIONS

"International Application Serial No. PCT/US2015/010452, International Preliminary Report on Patentability dated Jul. 21, 2016", 9 pgs.

"International Application Serial No. PCT/US2015/010452, International Search Report dated Apr. 2, 2015", 5 pgs.

"International Application Serial No. PCT/US2015/010452, Written Opinion dated Apr. 2, 2015", 7 pgs.

"Chinese Application Serial No. 201580012967.4, Office Action dated Feb. 5, 2018", (W/ English Translation), 13 pgs.

"European Application Serial No. 15701866.4, Communication Pursuant to Article 94(3) EPC dated Mar. 16, 2018", 4 pgs.

* cited by examiner

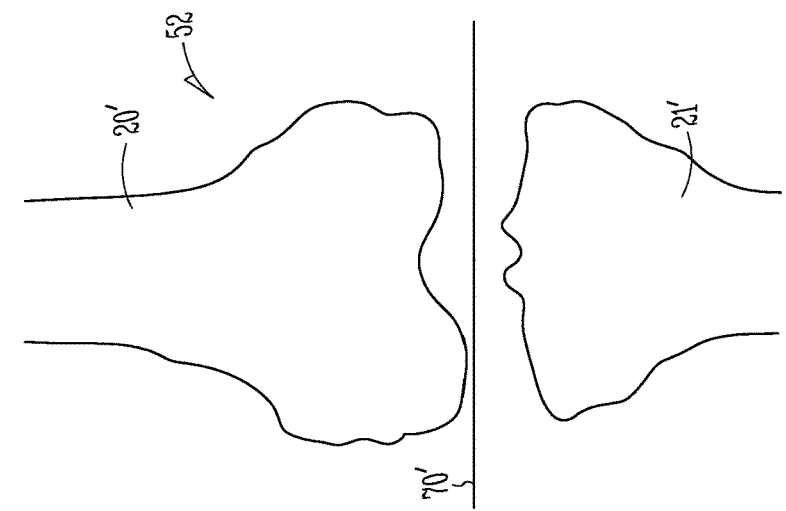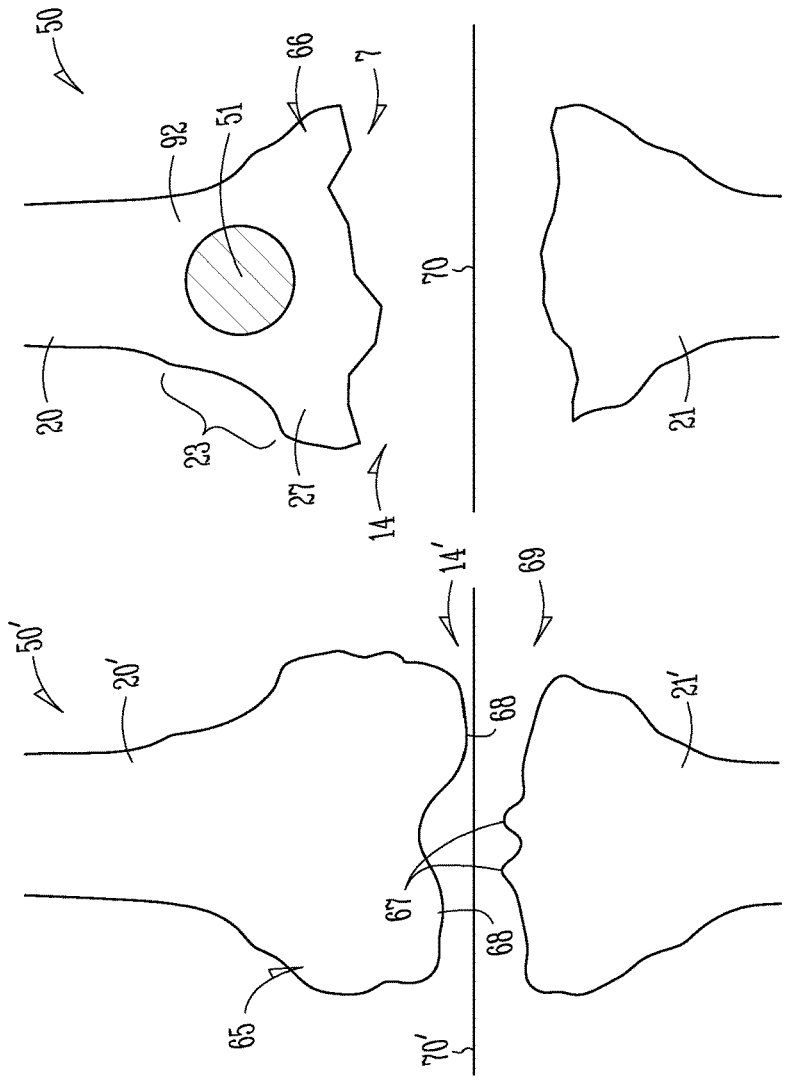

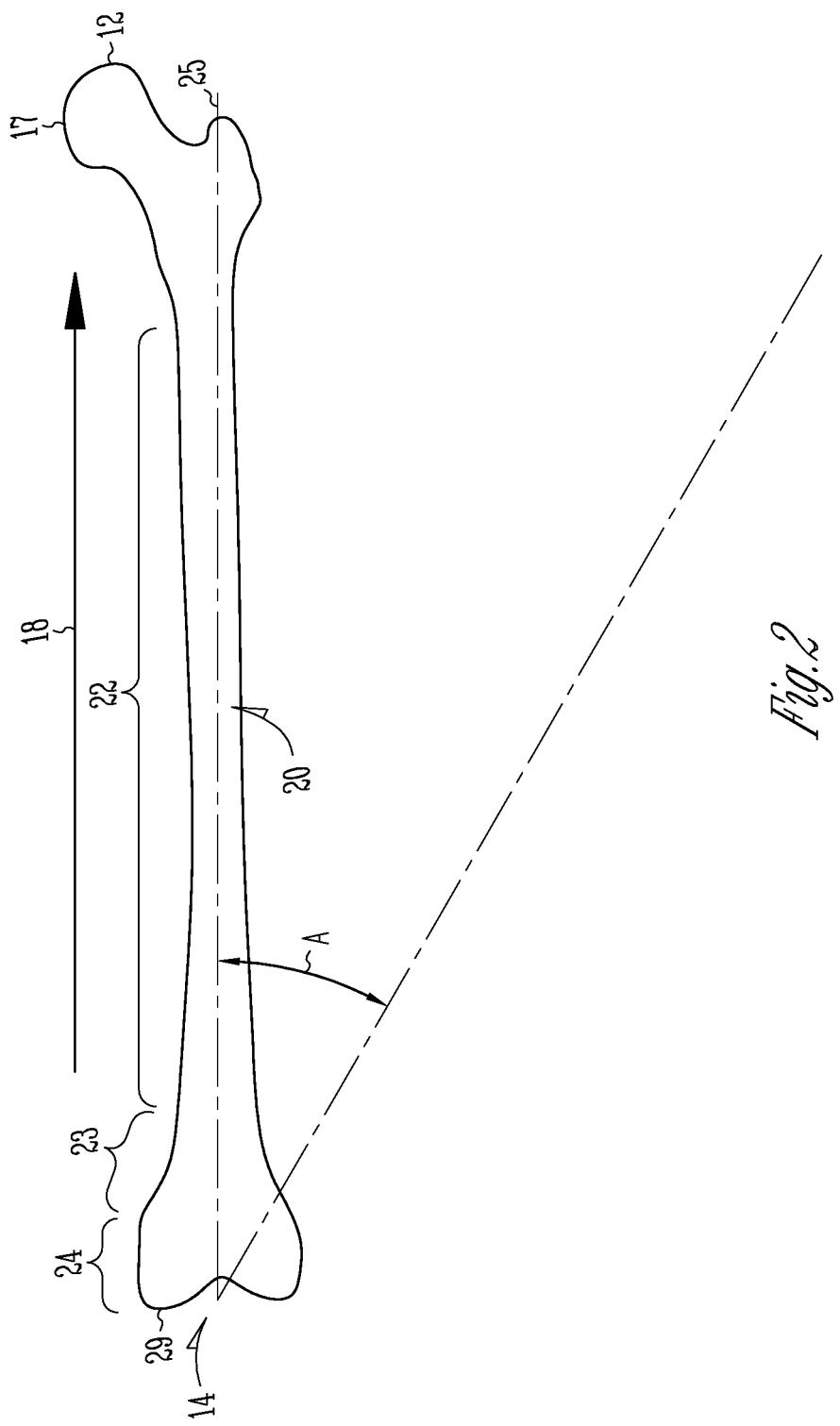

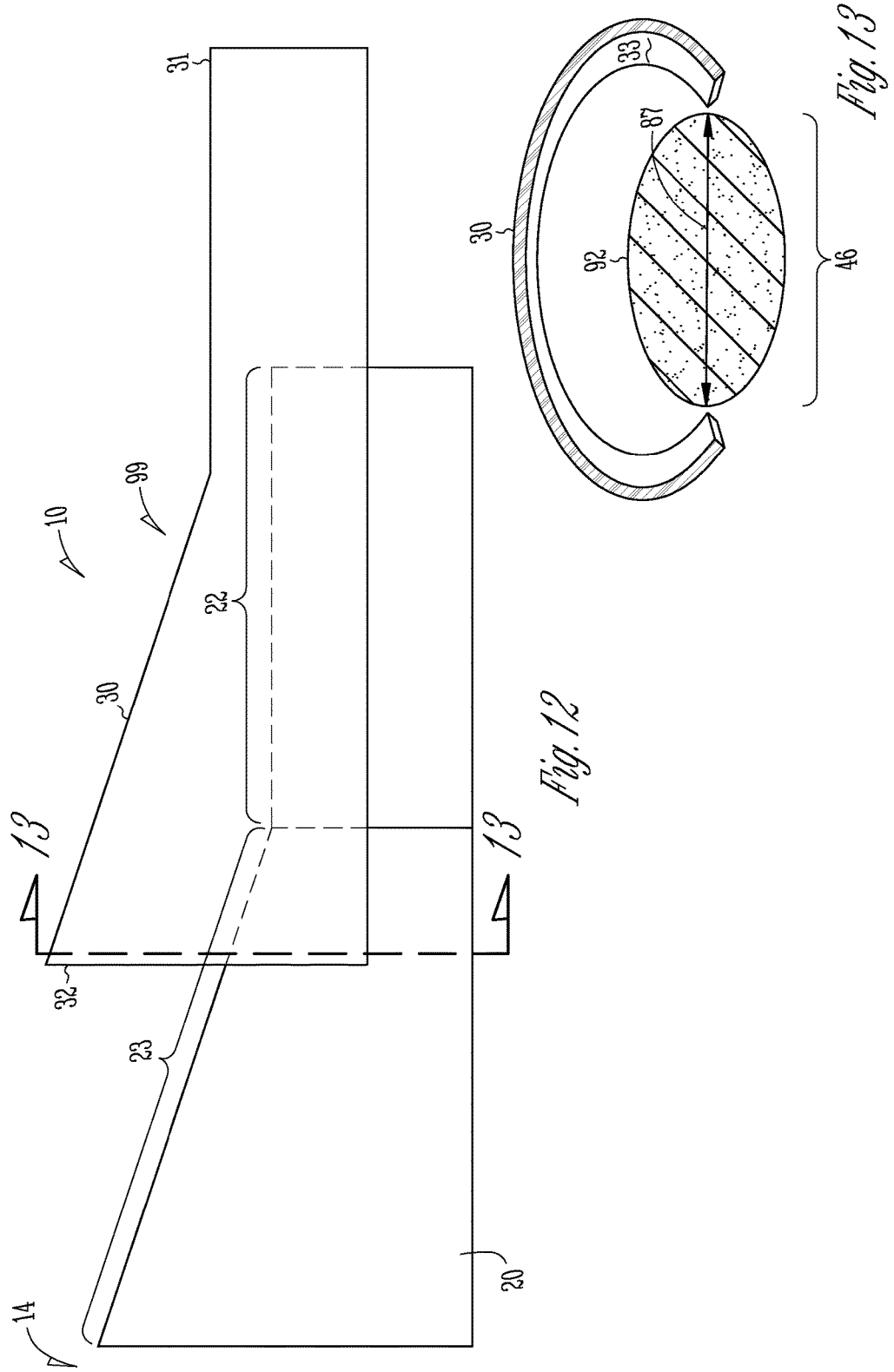

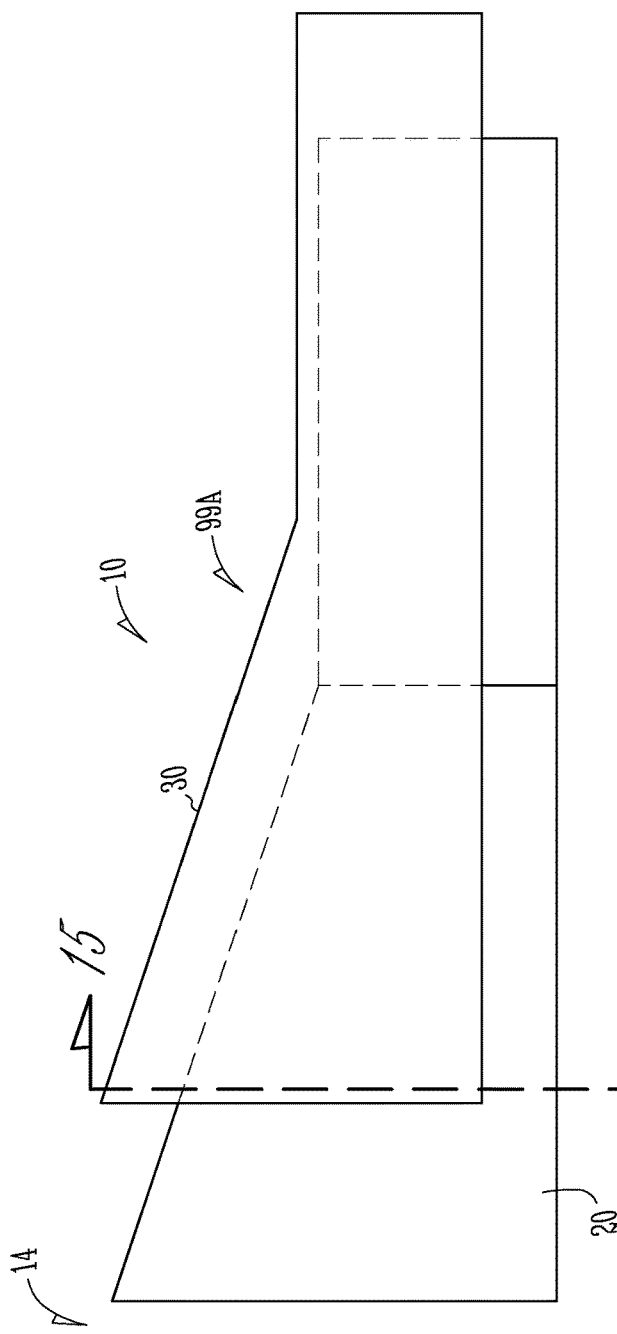
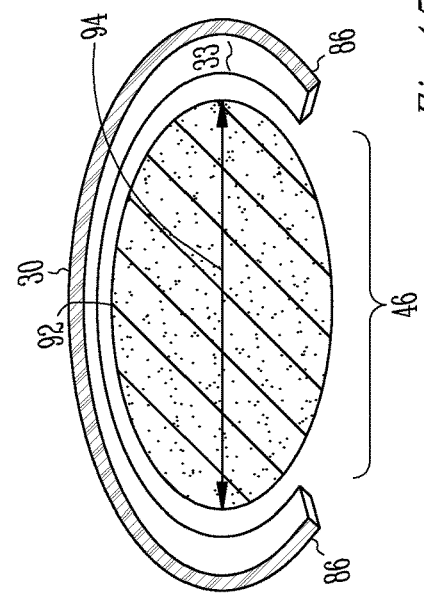

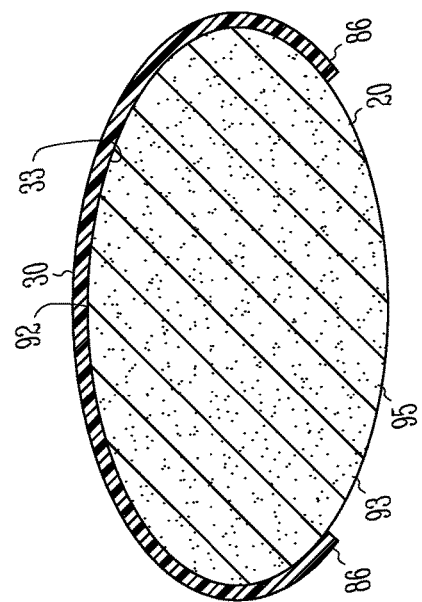
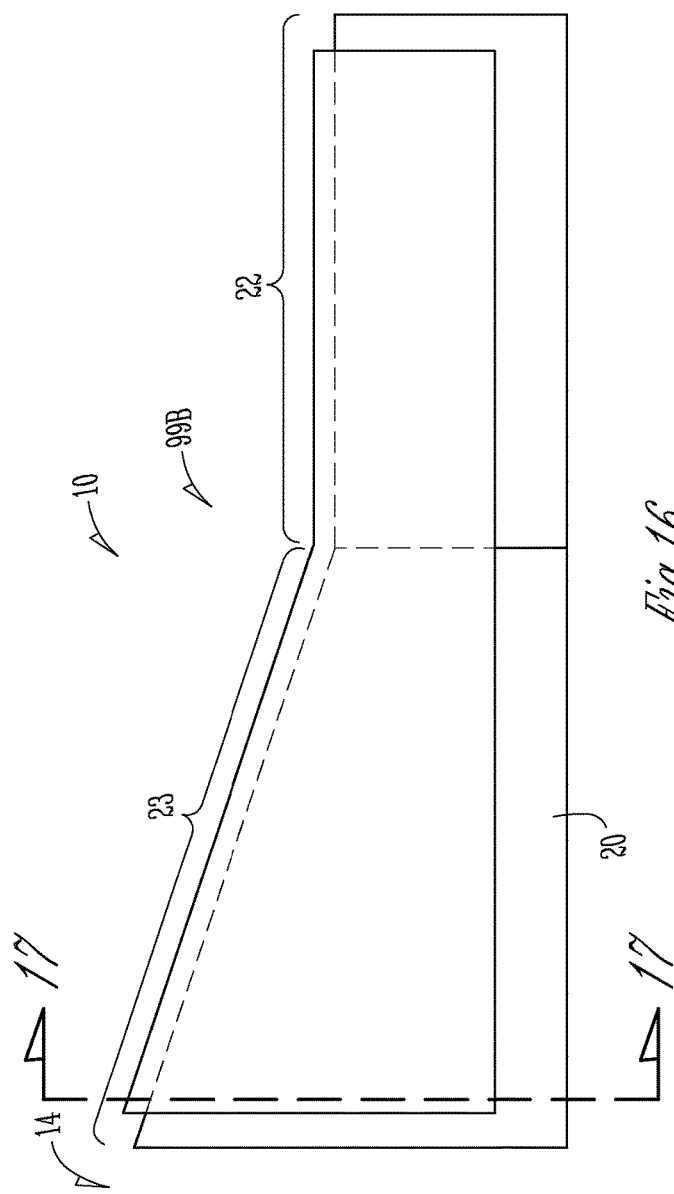

REVISION JOINT REPLACEMENT DEVICE AND METHOD

CLAIM OF PRIORITY

This application claims the benefit of U.S. Provisional Patent Application Ser. No. 61/925,305, filed on Jan. 9, 2014, the benefit of priority of which is claimed hereby, and which is incorporated by reference herein in its entirety.

TECHNICAL FIELD

This patent document pertains generally, but not by way of limitation, to a device and method to aid in installing an orthopedic implant in a revision surgery.

BACKGROUND

A revision surgery can be performed after an orthopedic implant has failed. The components of the implant may have worn out or broken, the patient body may have rejected the implant, or the bone and surrounding tissues may have become infected. Because the bones of the joint have already been altered due to the previous implant surgery, normal bone landmarks at the joint may no longer be present. In addition, conventional X-ray or Computed Tomography (CT) scanning can be highly affected by echoing resulting from metal implant parts; thus a clear scan of the bone area near the metal implant can be difficult or nearly impossible to obtain. A revision surgery can thus be challenging due to infection, patient discomfort, or difficulty in obtaining an accurate depiction of the bone near the joint line.

In a conventional revision surgery, in order to determine the final three dimensional positioning of an implant, an aperture can be drilled in the end of a femur for example for the placement of a femoral implant stem. A surgeon then needs to decide the "rotation" of the implant, in other words, twisting the implant or provisional about the stem and fixing a final rotational position. The surgeon must then decide how far in or out the implant should be placed in the stem hole. This positioning can determine the ultimate joint line of the implant.

OVERVIEW

The present inventors recognized that it would be beneficial to provide devices and methods for revision surgery that, in comparison to conventional revision surgery techniques, can lead to an accurate determination of the joint line and improved placement of a femoral stem of a femoral implant. The system and method of the present disclosure allows a surgeon to plan more of the revision surgery before operating on a patient. Preoperative planning can reduce the time required to complete the revision surgery and can improve placement of the revision implant. This disclosure provides a novel and unique device and method for providing a reference "landing zone" or reference location to aid in installing a revision implant. Also disclosed is a method for recreating normal joint lines and configurations in a surgical environment where normal bone configurations are damaged, missing or previously removed. Using the device and method disclosed herein, the final three dimensional positioning of the implant can be planned pre-operatively and built into a revision joint replacement device.

To further illustrate the revision joint replacement device and methods disclosed herein, a non-limiting list of examples is provided here:

In Example 1, a device to aid in performing a revision surgery on a joint, the device can comprise: a body member having a bone facing bottom surface, an opposing top surface, a first end portion configured to be disposed on a bone, and a second end portion opposite the first end portion and configured to be disposed on the bone nearer to the joint relative to the first end portion; a connecting member attached to the body member and configured to extend beyond an end of the bone at the joint; and a guide member attached to the connecting member and including an opening configured to receive a cutting tool, wherein the device is sized and shaped based on a computed tomography (CT) scan of the bone, and the guide member is configured so that when the device is installed on the bone, the longitudinal axis of the opening is aligned with a longitudinal direction of the bone.

In Example 2, the device of Example 1 can optionally be configured such that the body member can have at least one aperture formed in the body member that corresponds to at least one reference point for a bone cutting guide.

In Example 3, the device of Example 2 can optionally be configured such that the at least one reference point for the bone cutting guide includes a reference point for attaching a cutting guide used to set a joint line of a prosthetic implant.

In Example 4, the device of any one or any combination of Examples 2-3 can optionally be configured such that the at least one reference point for the bone cutting guide includes a reference point for attaching a cutting guide used to set a rotation of a prosthetic implant.

In Example 5, the device of any one or any combination of Examples 2-4 can optionally be configured such that the at least one reference point for the bone cutting guide is determined based on measurements of the bone from the CT scan and estimated dimensions of the bone using a digital library of bones, the estimated dimensions of the bone being unattainable from the CT scan.

In Example 6, the device of any one or any combination of Examples 2-5 can optionally be configured such that the at least one reference point for the bone cutting guide is determined based on a CT image of a healthy joint that is a mirror image of the joint.

In Example 7, the device of Example 6 can optionally be configured such that the joint is part of a left leg of a patient and the healthy joint is part of a right leg of the patient, or vice-versa.

In Example 8, the device of any one or any combination of Examples 1-7 can optionally be configured such that the device is sized and shaped based on a reference location on a computed tomography (CT) scan of the bone so that the bone facing bottom surface matches an external bone surface at a corresponding reference location on the bone.

In Example 9, the device of Example 8 can optionally be configured such that the body member includes a region with curvature on the bottom facing surface so that when the device is installed at the reference location, the curvature matches at least 50 per cent of a circumference of the bone at the reference location.

In Example 10, the device of any one or any combination of Examples 8-9 can optionally be configured such that the guide member is oriented so that when the device is installed at the reference location, the longitudinal axis of the guide member is offset from a longitudinal axis of a medullary canal of the bone.

In Example 11, the device of any one or any combination of Examples 1-10 can optionally be configured such that the body member is formed of at least one of a metal or metal alloy.

In Example 12, the device of any one or any combination of Examples 1-11 can optionally be configured such that the body member has a flare such that the first end portion of the body member is narrower than the second end portion of the body member, and the flare matches a flare of the bone.

In Example 13, the device of any one or any combination of Examples 1-12 can optionally be configured such that the bone is a femur.

In Example 14, the device of any one or any combination of Examples 1-13 can optionally be configured such that the bone is a tibia.

In Example 15, the device of any one or any combination of Examples 1-14 can optionally be configured such that the joint is a knee joint.

In Example 16, a system for performing a revision surgery on a knee joint, the system can comprise: a femoral implant configured to be installed on the bone so that a distal end of the implant approximates a normal joint line of the knee joint, the femoral implant including a stem; a bone plate including a body member having a bone facing bottom surface; an opposing top surface; a first end portion configured to be disposed on a bone, and a second end portion opposite the first end portion and configured to be disposed on the bone nearer to the joint relative to the first end portion; a connecting member attached to the body member and configured to extend beyond an end of the bone at the joint; and a cutting tool guide member attached to the connecting member and configured to guide forming of an aperture to prepare the bone to receive the stem of the femoral implant in a medullary canal region of the bone.

In Example 17, a method for performing a revision implant surgery, the method can comprise the steps of: performing a CT scan of a joint that includes a bone and an orthopedic implant attached to the bone, the CT scan performed prior to performing the revision implant surgery; determining a reference location on a surface of the bone based on images from the CT scan; forming a bone plate configured for attachment to the bone and configured to match a profile of the bone at or near the reference location, the bone plate including a guide member and at least one aperture formed in the bone plate; fixing the bone plate to the bone at the reference location, wherein when the bone plate is fixed to the bone, the guide member is aligned with a longitudinal direction of the bone; and preparing a canal of the bone to receive a stem of a revision implant by using the guide member to guide a cutting tool in the canal of the bone.

In Example 18, the method of Example 17 can optionally be configured to further comprise the step of: forming at least one aperture in the bone for attaching a cutting guide based on a location of the at least one aperture in the bone plate when the bone plate is fixed to the bone at the reference location.

In Example 19, the method of Example 18 can optionally be configured such that the location of the at least one aperture in the bone plate is based on a mirror image of a CT image of a healthy joint.

In Example 20, the method of any one or any combination of Examples 18-19 can optionally be configured such that the location of the at least one aperture in the bone plate is based on inputting CT scan measurements of the bone into a databank of bone measurements to estimate normal dimensions of the bone.

In Example 21, the method of any one or any combination of Examples 18-20 can optionally be configured such that the at least one aperture in the bone for attaching the cutting guide is used to set a joint line of an implant.

In Example 22, the method of any one or any combination of Examples 18-21 can optionally be configured such that the at least one aperture in the bone for attaching the cutting guide is used to set a rotation of a prosthetic implant.

In Example 23, the method of any one or any combination of Examples 17-22 can optionally be configured such that fixing the bone plate to the bone includes: placing the bone plate from a position that is located in a diaphysial direction from the reference location on the bone; and sliding the bone plate towards a metaphysis region of the bone until the bone plate locks onto the matching reference location.

In Example 24, a device to aid in performing a revision surgery, the device can comprise: a body member having a bone facing bottom surface; an opposing top surface; a first end portion configured to be disposed on a bone farther from the joint; a second end portion opposite the first end portion and configured to be disposed on the bone nearer to the joint, a portion of the bone facing bottom surface disposed on a metaphysis region of the bone; and a guide member connected to the body member and having a longitudinal axis aligned with a longitudinal direction of the bone, wherein the body member is configured to lock onto a specific reference location of the bone, the locking provided by a flared fit between the metaphysis region of the bone and the bone plate, and a perimeter of the body engaging at least 50% of a perimeter of the bone.

In Example 25, the revision joint replacement device, system, and method of any one or any combination of Examples 1-24 can optionally be configured such that all elements, operations, or other options recited are available to use or select from.

These and other examples and features of the revision joint replacement device and related method will be set forth in part in the following Detailed Description. This Overview is intended to provide non-limiting examples of the present subject matter—it is not intended to provide an exclusive or exhaustive explanation. The Detailed Description below is included to provide further information about the present insert press and related method.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

FIG. 1A illustrates an anterior view of a healthy knee joint.

FIG. 1B illustrates an anterior view of a knee joint needing a revision surgery.

FIG. 1C illustrates an anterior view of a mirror image of the healthy knee joint of FIG. 1A.

FIG. 2 illustrates a top view of a long bone, such as a femur.

FIG. 12 illustrates a side view of the revision surgery device of FIG. 10 in accordance with the present application.

FIG. 13 illustrates a cross sectional view of a portion of the revision surgery device of FIG. 12 in accordance with the present application.

FIG. 14 illustrates a side view of the revision surgery device of FIG. 10 in accordance with the present application.

FIG. 15 illustrates a cross sectional view of a portion of the revision surgery device of FIG. 14 in accordance with the present application.

FIG. 16 illustrates a side view of the revision surgery device of FIG. 10 in accordance with the present application.

FIG. 17 illustrates a cross sectional view of a portion of the revision surgery device of FIG. 16 in accordance with the present application.

DETAILED DESCRIPTION

Figure 3:
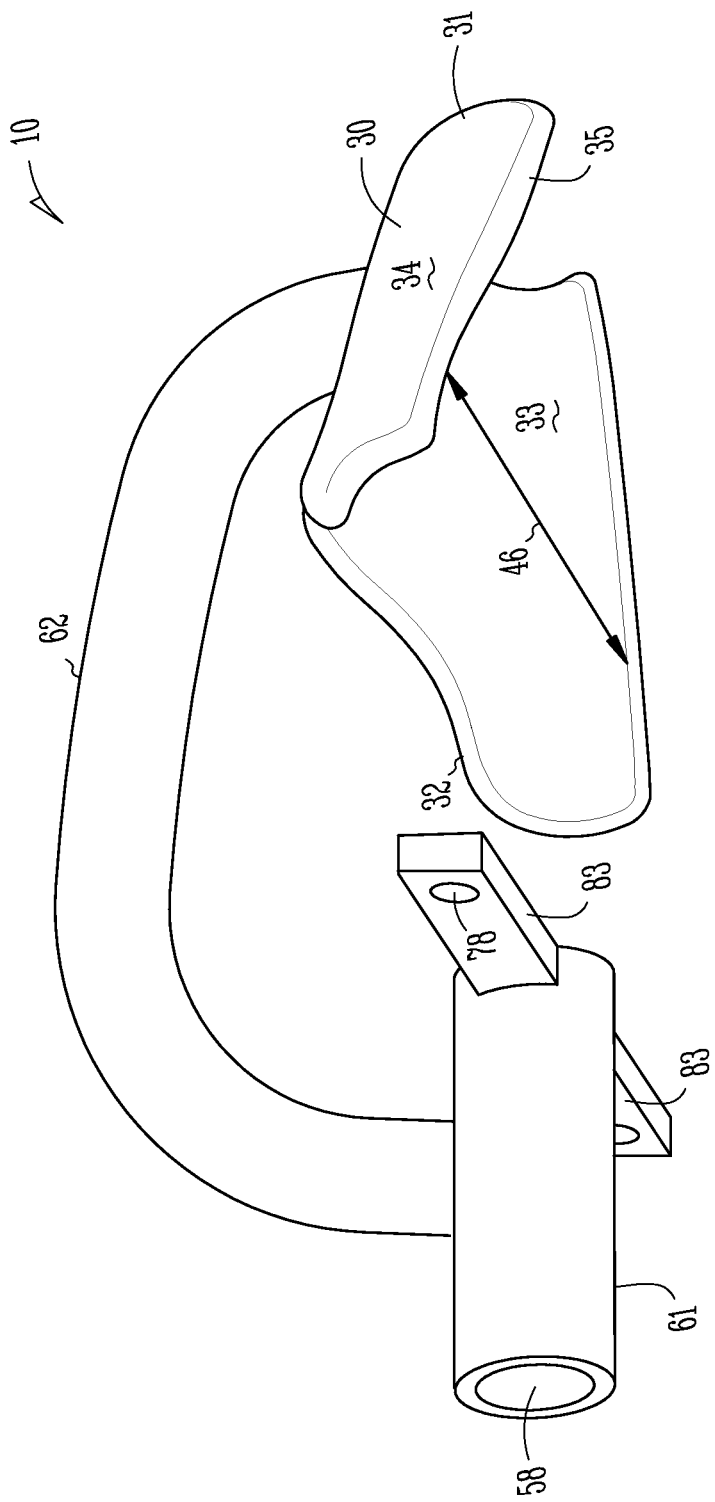
FIG. 3 illustrates an isometric bottom view of an example of a revision surgery device, in accordance with the present application.

The present disclosure uses CT scans or other comparable imaging processes to create a three dimensional model of a bone, which can provide a landing zone or distinct referencing location for a patient specific template or bone plate (a "device"). The model can be a virtual model, or a solid model created by conventional machining techniques or additive manufacturing techniques. The landing zone or referencing location can be located on a bone surface that has enough distance from metallic prosthetic components that have been installed on a previous surgery so that a clear and accurate CT scan can be obtained. The landing zone or referencing location can be located on a bone surface that has enough distance from damaged or infected tissue, so that the referencing location itself can remain intact throughout the revision surgery. For purposes herein, a long bone, such as a femur, is defined as having three basic regions—the diaphysis, the metaphysis and the epiphysis. The epiphysis is the area closest to the joint end of the bone and is usually the largest in diameter of the three regions. The diaphysis of the bone is a long narrow portion of the bone between the joint ends, and the metaphysis is a flared section that forms a transition between the narrower diameter diaphysis and the larger diameter epiphysis.

A device or "bone template" can be formed that can have a bone contacting surface that matches the landing zone of the 3D model of the bone site. The device can be formed so that it can be placed "above" or in a diaphysal direction from the landing zone and moved towards the joint until the device, because of its shape and matching features, can "lock on" to the landing zone. Because the device or template is referenced to actual locations on the 3D model, various apertures, cutting slots, and/or drill guides can be provided that can aid in fitting a prosthetic that has been planned for use in combination with the patient specific device. In an example, normal joint lines can be maintained by the revision prosthetic and missing bone can be replaced through the use of spacers, cones, augments or bone cement. As an example, the disclosed device and method can be configured to operate in conjunction with a particular prosthetic manufacturer and a particular manufacturer's method of installation.

FIG. 1A illustrates a depiction of a CT scan 50' of a right knee joint 65, which can include a femur 20' and a tibia 21'. The right knee joint 65 is healthy and has not been altered. A joint line 70' can be a central axis line that is generally transverse to the direction of the femur 20' and the tibia 21', making up a joint 14', which bends or flexes about the joint line 70'. Although a bone can have more than one "joint", in this document the joint 14' (or a joint 14) refers to the knee joint.

FIG. 1B illustrates a depiction of a CT scan 50 of a left knee joint 66, which can include a femur 20 and a tibia 21. The left knee joint 66 can require a revision surgery after removing a previously installed implant. When a surgeon is determining the joint line 70 for the revision implant, making additional cuts to remove infected or damaged tissue, or preparing the bone site 7, normal landmarks 69 provided by a healthy knee are missing (see FIG. 1A). These landmarks, which can be seen in the right knee joint 65, can include, for example, intercondyloid eminences 67 of the tibia 21' or the condyle ends 68 of the femur 20'. These landmarks are missing from the left knee joint 66, because the femur 20 and the tibia 21 have been previously altered to fit the original prosthetic.

FIG. 1C illustrates a depiction of a mirror image 52 of the CT scan 50' of FIG. 1A. The femur 20', tibia 21' and joint line 70' of FIG. 1A, which illustrate a healthy right knee 65, can be used to create a mirror image in FIG. 1C to approximate what a healthy left knee could look like. See below for further description of FIG. 1C.

FIG. 2 illustrates a femur 20 having a distal end 29 and a proximal end 12. The femur 20 shown in FIG. 2 can be the femur 20 of the damaged left knee 66 of FIG. 1B. For simplicity and reference, the femur 20 in FIGS. 2, 4-7, and 10-11, may not be illustrated as damaged as femur 20 of FIG. 1B. The femur 20, or any long bone for example, has three main regions: a diaphysis region 22, a long narrow portion between the distal end 29 and the proximal end 12 of the femur 20; the epiphysis region 24, a large end of the femur 20 closest to a joint 14 (formed between the femur 20 and a tibia, not shown); and a metaphysis region 23, a flared transition portion between the narrow diaphysis 22 and the larger epiphysis 24. The femur 20 can have a shape which can provide a longitudinal direction 18. The longitudinal direction 18 can be defined as a line collinear with or parallel to a longitudinal axis 25 of the femur 20, or within 30 degrees of the longitudinal axis 25, as in angle A.

FIG. 3 illustrates an isometric bottom view of a revision surgery device 10. The device 10 can include a body member 30 having a top surface 34 opposite a bone facing bottom surface 33. The body member 30 can extend from a first end portion 31 to a second end portion 32. A thickness 35 between the bone facing bottom surface 33 and the top surface 34 can be configured to give the body member 30 sufficient strength to allow firm fixation of the device 10 to a bone site 7, such as at a reference location 51 (see FIG. 1B). Fixation of the device 10 to the bone is described further below in references to FIGS. 4-7.

The contours of the bone facing bottom surface 33 can match the contours of an exterior surface 92 of the femur 20 (see FIG. 1B) such as at a pre-planned reference location 51 provided by 3D imaging. The shape and position of the reference location 51 is described further below and can be shaped or positioned in any desired manner or location. The device 10 can be manufactured from metals, metal alloys, plastics, polymers, composites, ceramics or any material with enough suitable strength to form a rigid or semi-rigid component. The device 10 can be manufactured by conventional machining and forming techniques, by additive manufacturing techniques, or by manual forming techniques.

The device can be virtually designed, encoded, or formed using virtual or real models of a patient's bone developed from CT, x-ray or other means of bone imaging as a template for creating the geometry of the bone facing bottom surface 33 of the device 10. The device 10 can be manually formed using a 3D model of a patient's bone as a template for the bone facing bottom surface 33 of the device 10. Apertures, drilling and/or cutting guides, referencing/indexing marks for a contemplated prosthetic surgery can be built into the device 10 using virtual or real models of a patient's bone as a template. Any apertures, drilling or cutting guides formed as part of the device 10 can maintain referencing that relates to an original reference location and to the 3D imaging scans which are directly related to the patient's actual bone geometry. These features of the device 10 are described further below.

The device 10 can include a connecting member 62 that can extend from the top surface 34 of the body member 30 and can extend beyond the second end portion 32 of the body member 30. The connecting member 62 can be attached or removable to the body member 30. The connecting member 62 can be integrally connected to the body member 30, or attached by other means such as threading, welding, gluing, bolting, pinning or other means known in the art. If the connecting member 62 is removable, it can be indexed so that a surgeon or technician can install the connecting member 62 to the body 30 in a precise position. The connecting member 62 can extend beyond the distal end 29 of the femur 20 (see FIG. 4). The connecting member 62 can have a circular, rectangular, flattened, oval or irregularly shaped cross-section. A guide member 61 can be attached to the connecting member 62. The guide member 61 can have a circular, rectangular, flattened, oval or irregularly shaped cross-section. The device 10 can include more than one connecting member 62 and each can attach to one or a plurality of guide members 61. For example, the guide member 61 can be supported by more than one extensions or connecting members 62 attached to the body 30.

The guide member 61 can include an opening 58 that is configured to receive and guide a cutting tool 57 (see FIG. 4), such as a drill, a reamer, a burr, a mill or any cutting tool known to those skilled in the art. The guide member 61 is described further below. A bracket member 83 can be attached to the guide member 61 and can include a rotation referencing guide 78 (described more fully below).

Figure 4:
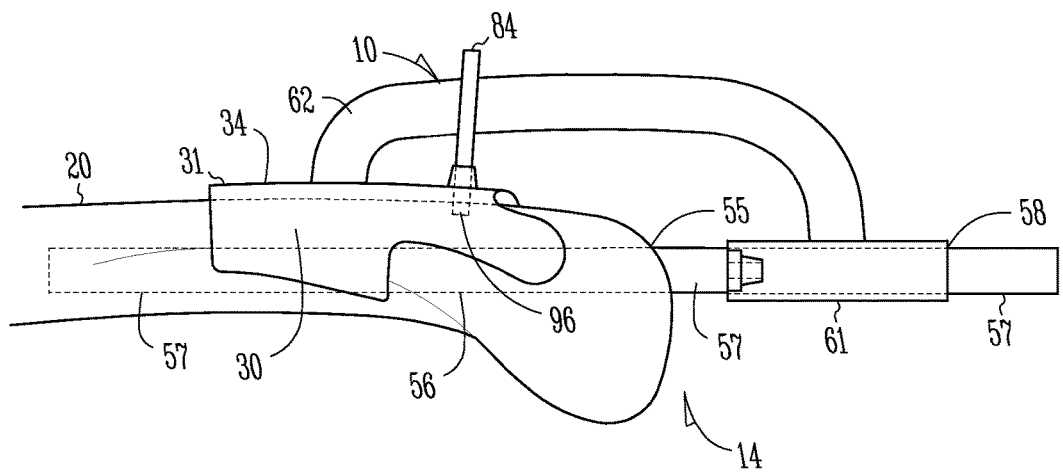
FIG. 4 illustrates a side view of the revision surgery device of FIG. 3 (disposed on a bone), in accordance with the present application.
Figure 5:
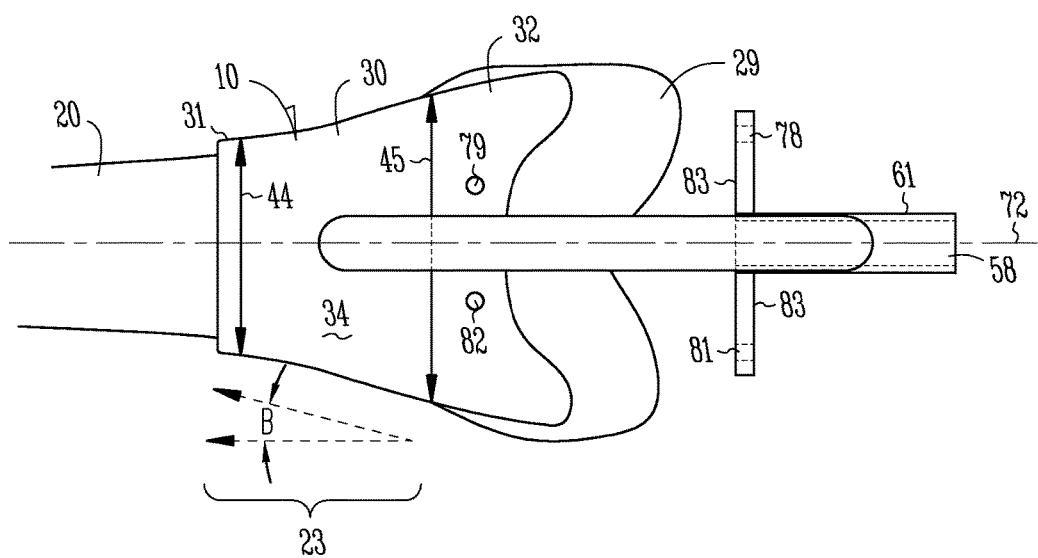
FIG. 5 illustrates a top view of the revision surgery device of FIG. 3 (disposed on a bone), in accordance with the present application.

FIGS. 4-7 are illustrations of the device 10 of FIG. 3 installed on the distal end 29 of the femur 20 of FIG. 2. Although the device 10 is illustrated as disposed on a femur 20, the device 10 can be used on any bone having a flared portion near a joint. In FIG. 4, the first end portion 31 can be disposed farther away from a joint 14 of the femur 20. The second end portion 32, opposite the first end portion 31, can be disposed nearer to the joint 14. As shown in FIG. 5, the first end portion 31 can include a first width 44, that can be generally transverse to the longitudinal axis 25 (see FIG. 2) of the femur 20. The second end portion 32 can include a second width 45, that can be generally transverse to the longitudinal axis 25 (see FIG. 2) of the femur 20. In an example, the first width 44 can be narrower than the second width 45 and the body 30 can include a flare angle B that matches or approximates a flare angle of the metaphysis region 23 of the femur 20.

As shown in FIGS. 4 and 5, the opening 58 of the guide member 61 can receive and guide a cutting tool 57 that can be used to create or enlarge an aperture 56 in the femur 20. The aperture can coincide with the medullary canal of the femur 20 or deviate from the medullary canal. The guide member 61 can be used with removable drill guides that can allow a small initial drill hole and the guide member 61 can be sized to receive reamers for a final implant stem size. In another example, final reaming for an implant stem can be accomplished with the device 10 removed from the femur 20. The position of the guide member 61 can be configured to match positions determined during pre-operative planning by a surgeon from 3D imaging. A position of the guide member 61 can be dependent upon the position of the body 30 on the femur 20. The body 30 can have one or more fixation apertures located at a particular position on the body 30 so that the body 30 can be securely fixed to the femur 20 before any bone cutting is performed using the guide member 61.

A position of the guide member 61 on the femur 20 can determine, in part, a starting position 55 of the aperture 56 in the femur 20. The position of the guide member 61 can determine the angle of the cutting tool 57 in an axial direction. An intramedullary pin can be placed in the aperture 56 and can be used as a reference for placement and positioning of bone cutting guides. The aperture 56 can be sized by reamers, drills or other cutting tools to provide a fit for the stem of a prosthetic implant or a provisional implant. The aperture 56 can form a reference axis line 72 (see FIG. 5).

Figure 6:
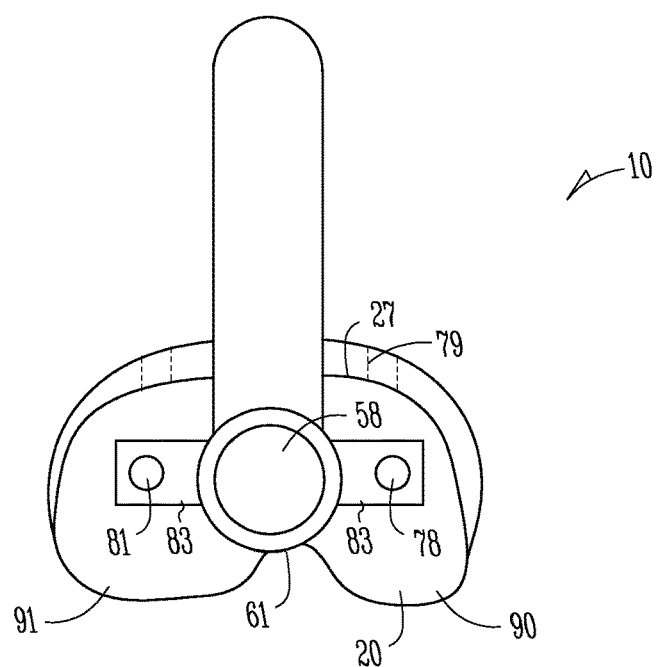
FIG. 6 illustrates a front view of the revision surgery device of FIG. 3 (disposed on a bone), in accordance with the present application.

FIGS. 5 and 6 further illustrate device 10 installed on the bone and shows a rotation referencing guide 78 and a joint line referencing guide 79. By using at least two additional reference points, such as the rotation referencing guide 78 and the joint line referencing guide 79, in addition to the reference axis line 72, a final implant position can be determined. The positioning of the two reference points 78 and 79 and the reference axis line 72 can be built into the device 10 with preoperative planning before the first incision of the revision surgery is performed. Because positioning of these referencing points can be planned pre-operatively, apertures for these referencing points can also be used to fix the device 10 to the femur 20, before forming or enlarging the aperture 56 or making any bone resections. The joint line referencing guide 79 can guide a cutting tool to provide an aperture in the anterior side 27 of the femur 20. A joint line referencing pin 84 can be received in a joint line aperture 96 (see FIG. 4) created using a joint line referencing guide, such as an additional joint line referencing guide 82 (described below).

Figure 9:
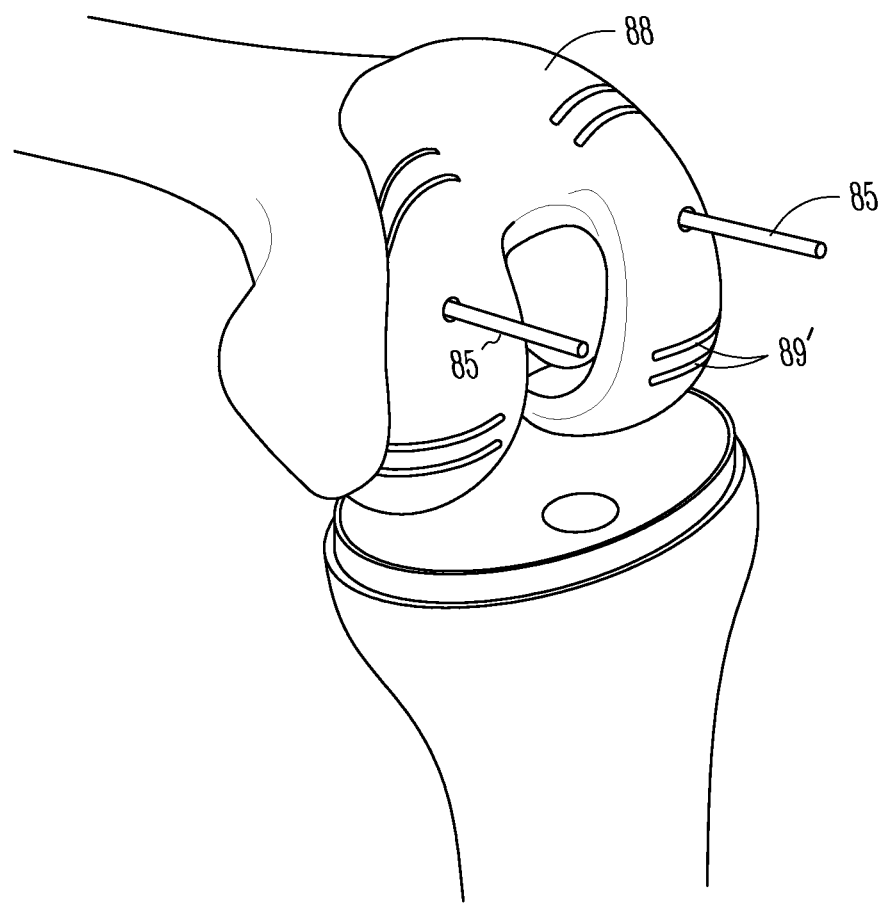
FIG. 9 illustrates an isometric view of an example of a cutting guide, in accordance with the present application.

The rotational referencing guide 78 can guide or position a drill, reamer or other cutting tool and provide an aperture for fixing positional rotation of a cutting guide or prosthetic component about the reference axis line 72 (see FIG. 9). In an example, an additional rotation referencing guide 81 can be provided that can provide a slightly different rotational positioning, allowing fine tuning options for the surgeon. The additional rotation referencing guide 81 can also match rotational positioning of the rotation referencing guide 78 to provide greater accuracy or stability. The rotation referencing guide 78, can be included in the bracket member 83 that can be attached to the guide member 61. Structures such as brackets, lobes, or extensions can include or support the rotation referencing guide 78, or any additional rotation referencing guides, such as aperture 81, and can also extend from other portions of the body 30 such as from the second end portion 32.

The joint line referencing guide 79 can guide or position a drill, reamer or other cutting tool and provide an aperture in the femur 20 for fixing a position along the reference axis line 72. If a surgeon or technician determines that the joint line 70 (see FIG. 8) formed by the revision implant should be farther from the distal end 29 of the femur 20 in a proximal direction, the joint line referencing guide 79 can be positioned accordingly during preoperative planning. The joint line referencing guide 79 can determine how far in or out (proximally or distally) a stem of a femoral implant or provisional is positioned in the aperture 56 (see FIG. 4). In an example, an additional joint line referencing guide 82 can be provided that can provide a slightly different joint line positioning, allowing fine tuning options for the surgeon. The additional joint line referencing guide 82 can also match joint line positioning of the joint line referencing guide 79 to provide greater accuracy or stability.

The referencing features described herein (the reference axis line 72, the rotation referencing guide 78 and the joint line referencing guide 79) can be configured to operate with a particular manufacturer's prosthetic component installation process. Additional referencing guides such as apertures 82 or 81 can be provided in any possible combination to give an operating surgeon as many options as possible during a surgical procedure. As described above, because the reference axis line 72, the rotation referencing guide 78, and the joint line referencing guide 79 can be built into the device 10, a three dimensional positioning of an implant or provisional in relation to the femur 20 can be determined once the device 10 "locks on" to a reference location 51, as described further below. In other words, the present disclosure provides a device 10 and method for locating a revision implant (or provisional implant) in three dimensional space in relation to the bone by determining the reference axis line 72, which can become the axis of a femoral stem of the revision implant. The device 10 can establish the "twist" in the femoral stem through the rotational referencing guide 78 and can also establish the proximal/distal location of the femoral stem along the reference axis line 72, through the joint line referencing guide 79.

Figure 7:
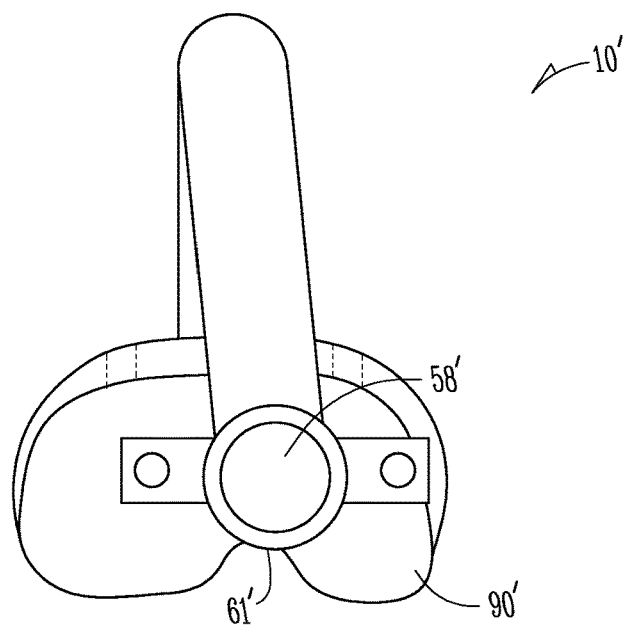
FIG. 7 illustrates a front view of the revision surgery device of FIG. 3 (disposed on a bone), in accordance with the present application.

FIGS. 6 and 7 illustrate how the rotation referencing guide 78 can relate to the opening 58 of the guide member 61. The opening 58 can provide the longitudinal axis 72 (see FIG. 5) about which the rotational referencing guide 78 can be positioned and ultimately control the rotational position of an implant or provisional implant about the stem of the implant. Implant component manufacturers can provide implant components with offset stems. Such offset stems can provide flexibility for implant procedures for irregular bone configurations. A bone may be bowed or have other features that may require a surgeon to use a prosthetic component with an offset stem feature. The surgeon can plan such an offset position into the device 10 in designing a location of the guide member 61 on the device 10. The guide member 61 in FIG. 6 can be centrally located between a medial condyle 90 and a lateral condyle 91. In planning for an offset stem, a guide member 61', and an opening 58' can be constructed to be offset as illustrated in FIG. 7 and be located, for example, more towards the medial condyle 90' (or in whatever offset position is desired).

Referring again to FIG. 1B, in pre-operative planning a surgeon can work with 3D images, such as a CT scan or a bone model created from such a bone scan. Because the normal landmarks 69 (see FIG. 1A) of the end of the femur 20 are not present in the case of a femur undergoing revision, the surgeon can use a 'landing zone" or reference location 51 that can be on another surface of the bone, for example the anterior side 27 of the femur 20 in the metaphysis region 23. Once this landing zone or reference location 51 has been determined, other reference points and locations can be measured and determined from the initial reference location 51. The body member 30 of the device 10 can be formed so that a bone facing bottom surface 33 (see FIG. 3) can match the exterior surface 92 of the femur 20.

During the placement and fitting of a prosthetic implant there can be two referencing procedures that can include 1) determination of the joint line and 2) rotation of the prosthetic in relation to the rotational axis of the reference axis line 72 as described in FIG. 5. As discussed above and referring to FIGS. 1A-1C, the surgeon cannot use conventional bone or joint landmarks 69, because the joint 14 has been greatly altered by the previous implant surgery. One method that can be used to determine a joint line of a joint requiring revision surgery, such as the left knee joint 66 of FIG. 1B, can be by creating a mirror image 52 of an image scan 50' of a healthy right knee 65. If a patient has an analogous matching joint that is healthy, for example a healthy right knee 65; a mirror image 52 of the CT scan 50' of the right knee 65 can be created which can approximate what a healthy left knee could look like, even though the left knee 66 has been altered considerably by a previous implant surgery. The mirror image 52 of FIG. 1C can include the same joint line 70' that is present in FIG. 1A in relation to the right knee 65. The mirror image 52 can aid in determining the positioning of the joint line 70 in relation to the femur 20 on the left knee 66 and in relation to a reference location 51. Such estimation can allow formation and/or placement of referencing apertures on the body member 30 of the device 10 such as the joint line referencing guide 79 (see FIG. 5).

Maintaining the joint line in a revision surgery can provide a beneficial surgical outcome. Even though much of the bone can be removed from an initial implant surgery or the revision surgery, the missing bone can be replaced by augments, spacers, cones, cement, or any other means known to those skilled in the art to build up or replace missing bone material and keep the outer dimensions of prosthetic components as close to the normal joint line as necessary.

In some revision surgeries, there may be no matching healthy joint such as the right knee 65 in FIG. 1A for producing the mirror image 52 of FIG. 1C. For example, patients that have had a double knee replacement do not have an un-resected knee joint. In these cases, the surgeon can input measurements obtained from a CT scan or other imaging of the femur 20 (see FIG. 1B) such as, for example, diameters at various locations on the bone, or distances from landmarks that do exist, such as the head 17 of the femur 20 (see FIG. 2). Many measurements can be taken from imaging of the resected femur 20 and these measurements can be used in combination with a digital library that includes a databank of measurements from numerous representative bones. By comparing measurements taken from the resected femur 20 in FIG. 1B, to numerous representative bones, computer software can estimate what the length of the patient's bone was before any bone had been removed. Once the estimated normal length of the bone has been obtained, a joint line 70 can be accurately estimated.

Figure 8:
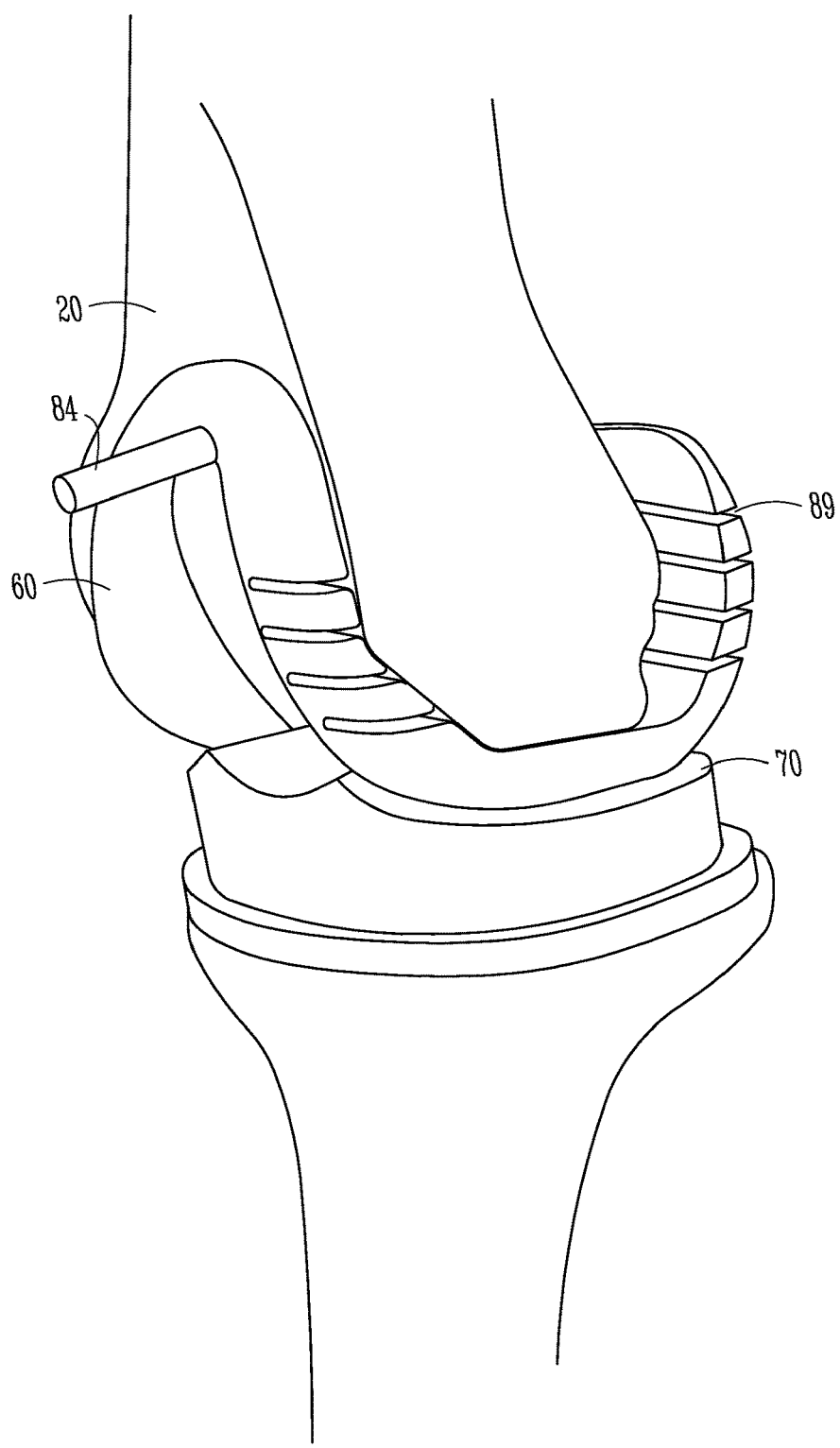
FIG. 8 illustrates an isometric view of an example of a cutting guide, in accordance with the present application.

FIG. 8 illustrates a cutting guide 60 positioned on the femur 20. In an example, the cutting guide 60 can also serve as a provisional implant. In a revision surgery, a surgeon can place provisional implants on the femur 20 to gauge a final implant position. Although the cutting guide 60 is shown in FIG. 8, this view can also approximate how a provisional implant or implant would appear in the final implant position. A joint line referencing pin 84 can be installed in the femur 20 to provide positioning for the cutting guide 60. The joint line referencing pin 84 can be installed in an aperture formed using the joint line referencing guide 79 as described above (see FIGS. 4 and 5). Placement of such a reference point either closer or farther from the existing end of the femur 20 can control final positioning of the joint line 70. Such a joint line referencing pin 84 can also be utilized to position a cutting guide 60 that can be used to prepare the femur 20 for a prosthetic implant by shaping the bone or removing unwanted bone material. In some instances more than one joint line referencing pin 84 can be used. The cutting guide 60 can provide numerous slots 89 that can serve as cut guides for making resections in the bone to fit an implant or in preparation for differently sized spacers or augments.

FIG. 9 illustrates a cutting guide 88 positioned on the femur 20. A rotational referencing pin 85 can be installed in the femur 20 to provide positioning for the cutting guide 88. The rotational referencing pin 85 can be installed in an aperture formed using the rotational referencing guide 78 as described above (see FIG. 5). Placement of such a reference point can control final rotational positioning of the cutting guide 88 that can be used to prepare the femur 20 for a prosthetic implant by shaping the bone or removing unwanted bone material. In some instances more than one rotational referencing pin 85 can be used. The cutting guide 88 can provide numerous slots 89' that can serve as cut guides for making resections in the bone to fit an implant or in preparation for differently sized spacers or augments.

Figure 10:
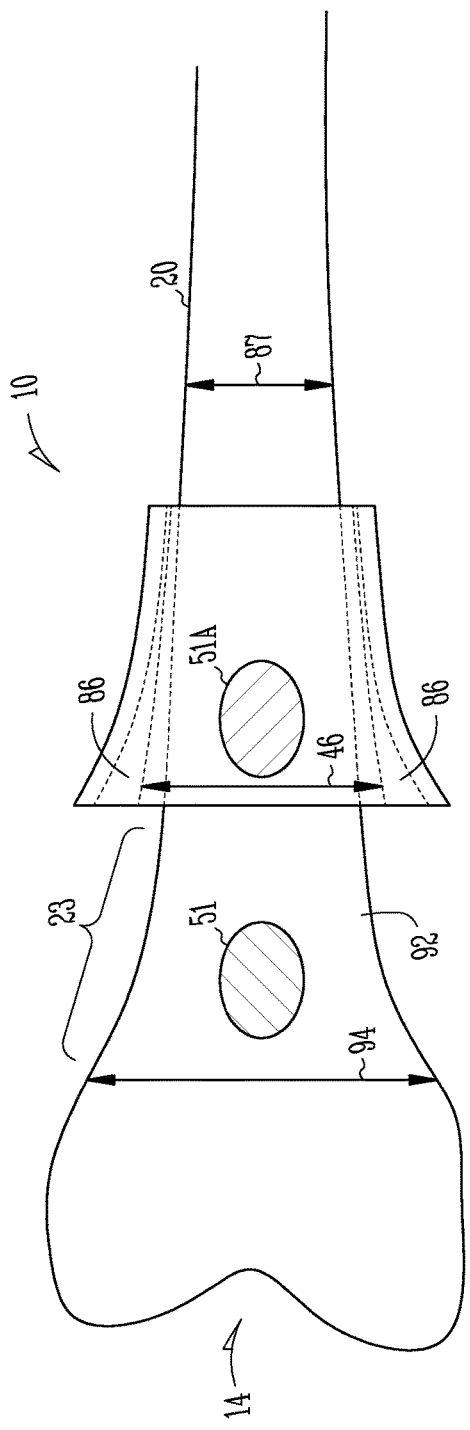
FIG. 10 illustrates a top view of an example of a revision surgery device as constructed in accordance with the present application.

In FIGS. 10-17, device 10 is the device 10 of FIGS. 3-6 except that for simplicity, the connecting member 61 and assorted features are not shown. FIG. 10 illustrates how a device 10 "locks on" to a reference location 51 that is pre-operatively picked by a surgeon on a 3D imaging scan of the femur 20. The surgeon can place the device 10 on the femur 20 at a location in a direction away from the joint 14. The device 10 can have a bottom opening 46 (see also FIG. 3) that is wide enough that the device 10 can be placed on the bone exterior surface 92 in an area where a first bone width 87 is smaller than the bottom opening 46. A matching reference location 51A is shown on the device 10 and can correspond to the reference location 51 on the femur 20. The device 10 can be slid towards the joint 14. In the flared metaphysis region 23, a second bone width 94 can be greater than the bottom opening 46 and because lower lobes 86 of the body 30 can be underneath the bottom half of the femur 20, the device 10 cannot be lifted directly up off the femur 20, once the device 10 has been slid far enough towards the joint 14.

Figure 11:
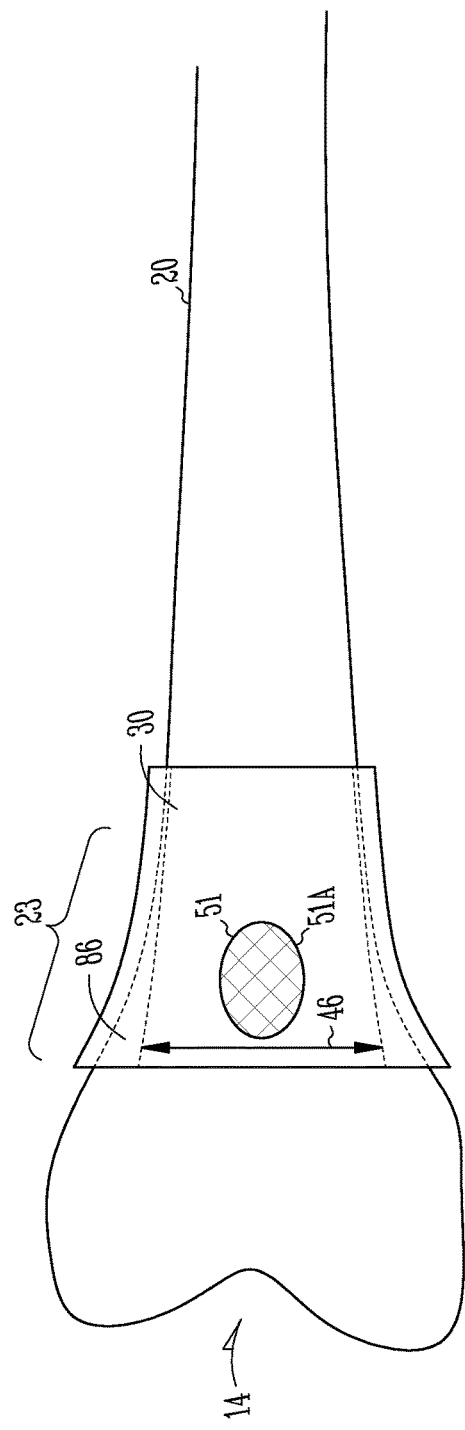
FIG. 11 illustrates a top view of the revision surgery device of FIG. 10 in accordance with the present application.

FIG. 11 is an example of the device 10 moved all the way towards the joint 14. Because of matching flares between the device 10 and the metaphysis region 23 of the femur 20, the device 10 cannot move any farther towards the joint 14. Because contours of the bone facing bottom surface 33 (see FIG. 3) are configured to match an exterior surface 92 (see FIG. 10) of the femur 20, the device 10 can fit the femur 20 at the reference location 51 like a hand-in-glove or like a contoured piece of a jigsaw puzzle. The exterior surface 92 of the femur 20 is not perfectly round, but can have an elliptical shape or flattened sections that can prevent the device 10 from any rotational movement about the longitudinal axis 25 (see FIG. 2) of the femur 20. The reference location 51 and the matching reference location 51A can coincide and the device 10 can be temporarily fixed to the femur 20.

FIGS. 12-17 provide different viewpoints of how the device 10 is "locked on" to the reference location 51 of the femur 20. As previously described, the diaphysis region 22 of the femur 20 can be narrower than the wider flared metaphysis region 23. The device 10 can be placed on the femur 20 at a location 99 far enough away from the joint 14 so that the first bone width 87 is less than the bottom opening 46 as in FIG. 13. At such a location, the bone facing bottom surface 33 can be lowered to engage the bone exterior surface 92 and the device 10 can be slid towards the joint 14.

In FIG. 14 the device 10 can be moved to location 99A and as shown in FIG. 15 a second bone width 94 can be wider than the bottom opening 46. Because the device 10 has not yet reached the reference location 51 of the femur 20, the bottom facing surface 33 is not tightly matching the exterior bone surface 92. Lower lobes 86 of the body 30 that are hidden in FIGS. 10 and 11 can be seen in FIGS. 15 and 17.

In FIG. 16 and the related cross sectional view, FIG. 17, the device 10 is shown at location 99B and cannot move any farther towards the joint 14 because of the matching flares between the bone facing bottom surface 33 and the bone exterior surface 92 of the metaphysis region 23. As a surgeon slides the device 10 towards the joint 14 he can feel the point when the device 10 cannot be moved any farther towards the joint 14. The femur 20 can have an elliptical shape 93 or have flattened features that are matched by the bone facing bottom surface 33. The matching features can prevent the device 10 from any rotational movement about the longitudinal axis 25 (see FIG. 2) of the femur 20. FIG. 17 illustrates the close fit between the bone facing bottom surface 33 and the bone exterior surface 92 after the body 30 has reached the reference location 51 (see FIG. 11). The circumference or perimeter of the body 30 can enclose or surround more the 50 percent of the circumference or perimeter of the femur 20. The lobes 86 can be disposed on a lower half 95 of the femur 20.

Although many of the examples disclosed in this document relate to femoral prosthetics, the revision joint replacement device and methods disclosed in this document can be used in prosthetic devices or methods relating to any joint of a human or animal body.

The above Detailed Description includes references to the accompanying drawings, which form a part of the Detailed Description. The drawings show, by way of illustration, specific embodiments in which the present insert press and method can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the term "patient" is intended to include mammals, such as for human applications or veterinary applications.

In the appended claims, the terms "including" and "in which" are used as the plain-English equivalents of the respective terms "comprising" and "wherein." Also, in the following claims, the terms "including" and "comprising" are open-ended, that is, an assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed:

1. A device to aid in performing a revision surgery on a joint, the device comprising:
    a body member having a bone facing bottom surface, an opposing top surface, a first end portion configured to be disposed on a bone, and a second end portion opposite the first end portion and configured to be disposed on the bone nearer to the joint relative to the first end portion, wherein the body member is configured to lock onto a specific reference location of the bone, the locking provided by a flared fit between a metaphysis region of the bone and the body member, and a perimeter of the body member at the flared fit engaging at least 50% of a perimeter of the bone;
    a connecting member attached to the body member at a first end and extending away from the body member so as to be configured to space a second end of the connecting member away from the bone beyond an end of the bone at the joint; and
    a guide member attached to the second end of the connecting member and including an opening configured to receive a cutting tool, wherein the body member is sized and shaped based on a computed tomography (CT) scan of the bone, and the guide member is configured so that when the body member is installed on the bone, a longitudinal axis of the opening is aligned with a longitudinal direction of the bone.

2. A device to aid in performing a revision surgery on a joint, the device comprising:
    a body member having a bone facing bottom surface, an opposing top surface, a first end portion configured to be disposed on a bone toward a diaphysis region of the bone, and a second end portion opposite the first end portion and configured to be disposed toward an epiphysis region of the bone nearer to the joint relative to the first end portion, wherein the body member is contoured to mate with a landing zone in the metaphysis region of the bone of the joint, the landing zone comprising a location on the bone that is both away from surfaces of the bone prepared to receive a prosthetic device and away from damaged or infected tissue of the bone identified in a computed tomography (CT) scan of the bone, the contour including a medial-lateral curvature to partially wrap around the bone;
    a connecting member releasably attached to the body member and configured to extend beyond an end of the bone at the joint; and
    a guide member attached to the connecting member and including an opening configured to receive a cutting tool, wherein the body member, connecting member and guide member are sized and shaped based on the computed tomography (CT) scan of the bone so that when the device is installed on the bone, a longitudinal axis of the opening is aligned with a longitudinal direction of the bone.

3. The device of claim 2, wherein the body member has at least one aperture formed in the body member that corresponds to at least one reference point for a bone cutting guide, a location for each aperture being determined based on the CT scan of a healthy joint that is a mirror image of the joint.

4. The device of claim 2, wherein the body member has a flare such that the first end portion of the body member is narrower than the second end portion of the body member, and the flare matches a flare of the bone, flaring outward as the body extends from the diaphysis region of the bone toward the second end portion proximate the epiphysis end.

5. The device of claim 2, wherein the body member is configured to lock onto a specific reference location of the bone, the locking provided by a flared fit between a metaphysis region of the bone and the body member, and a perimeter of the body member at the flared fit engaging at least 50% of a perimeter of the bone.

6. The device of claim 2, wherein the bone facing bottom surface of the body member is sized and shaped based on the CT scan of the bone to include contouring to match contours of an exterior surface of the diaphysis region of the bone.

7. A device to aid in performing a revision surgery on a joint including a bone extending along a major axis, the bone comprising a long bone, the device comprising:
    an elongate body member having a bone facing bottom surface, an opposing top surface, a first end portion configured to be disposed on the bone, and a second end portion opposite the first end portion and configured to be disposed on the bone nearer to the joint relative to the first end portion, wherein a portion of the bone facing bottom surface is configured to mate with a metaphysis region of the bone away from an epiphysis region of the bone such that the first end portion and the second end portion are elongated to extend in a direction parallel to the major axis;
    an arcuate connecting member releasably attached to the elongate body member at a first end and extending away from the elongate body member so as to be configured to space a second end of the arcuate connecting member away from the bone beyond an end of the bone at the joint; and
    a tubular guide member rigidly attached to the second end of the arcuate connecting member and including an opening configured to receive a cutting tool, wherein the elongate body member is sized and shaped based on a computed tomography (CT) scan of the bone, and the tubular guide member is configured so that when the elongate body member is installed on the bone, a longitudinal axis of the opening is aligned with a longitudinal direction of the bone parallel to the major axis.

8. The device of claim 7, wherein the elongate body member has at least one aperture formed in the elongate body member that corresponds to at least one reference point for a bone cutting guide.

9. The device of claim 8, wherein the at least one reference point for the bone cutting guide includes at least one of a joint line reference point for attaching a cutting guide used to set a joint line of a prosthetic implant and a rotation reference point for attaching a cutting guide used to set a rotation of a prosthetic implant.

10. The device of claim 8, wherein the at least one reference point for the bone cutting guide is determined based on measurements of the bone from the CT scan and estimated dimensions of the bone using a digital library of bones, the estimated dimensions of the bone being unattainable from the CT scan.

11. The device of claim 8, wherein the at least one reference point for the bone cutting guide is determined based on a CT image of a healthy joint that is a mirror image of the joint.

12. The device of claim 11, wherein the joint is part of a left leg of a patient and the healthy joint is part of a right leg of the patient, or vice-versa.

13. The device of claim 7, wherein the elongate body member is sized and shaped based on a reference location on the computed tomography (CT) scan of the bone so that the bone facing bottom surface matches an external bone surface at a corresponding reference location on the bone.

14. The device of claim 13, wherein the elongate body member includes a region with curvature on the bottom facing surface so that when the elongate body member is installed at the corresponding reference location, the region with curvature matches at least 50 percent of a circumference of the bone at the reference location.

15. The device of claim 13, wherein the tubular guide member is oriented so that when the elongate body member is installed at the corresponding reference location, the longitudinal axis of the tubular guide member is offset from and parallel to a longitudinal axis of a medullary canal of the bone.

16. The device of claim 7, wherein the elongate body member has a flare such that the first end portion of the elongate body member is narrower than the second end portion of the elongate body member, and the flare matches a flare of the bone extending in a direction of the major axis.

17. The device of claim 7, wherein the bone is a femur.

18. The device of claim 7, wherein the bone is a tibia.

19. The device of claim 7, wherein the body member is configured to lock onto a specific reference location of the bone, the locking provided by a flared fit between a metaphysis region of the bone and the body member, and a perimeter of the body member at the flared fit engaging at least 50% of a perimeter of the bone.

20. The device of claim 7, wherein the connecting member is releasably attached to the body member and the guide member.

21. The device of claim 7, wherein the bone facing bottom surface is contoured to mate with a landing zone on the bone comprising a location on the bone that is both away from surfaces of the bone prepared to receive a prosthetic device and away from damaged or infected tissue of the bone identified in the CT scan.

* * * * *